(12) United States Patent
Hernandez Altamirano et al.

(10) Patent No.: US 11,014,875 B2
(45) Date of Patent: May 25, 2021

(54) HYDROXYSULTAINE- AND SULFOBETAINE-BASED GEMINAL ZWITTERIONIC LIQUIDS, METHOD FOR OBTAINING SAME, AND USE THEREOF AS WETTABILITY MODIFIERS HAVING CORROSION INHIBITING PROPERTIES

(71) Applicant: INSTITUTO MEXICANO DEL PETRÓLEO, Mexico City (MX)

(72) Inventors: Raül Hernandez Altamirano, Mexico City (MX); Violeta Yasmin Mena Cervantes, Mexico City (MX); Luis Silvestre Zamudio Rivera, Mexico City (MX); César Andrés Flores Sandoval, Mexico City (MX); Alejandro Ramírez Estrada, Mexico City (MX); Rodolfo Cisneros Devora, Mexico City (MX); José Manuel Martínez Magadan, Mexico City (MX); Raúl Oviedo Roa, Mexico City (MX); Jorge Francisco Ramírez Pérez, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 395 days.

(21) Appl. No.: 15/535,323

(22) PCT Filed: Nov. 27, 2015

(86) PCT No.: PCT/MX2015/050001
§ 371 (c)(1),
(2) Date: Jun. 12, 2017

(87) PCT Pub. No.: WO2016/093688
PCT Pub. Date: Jun. 16, 2016

(65) Prior Publication Data
US 2017/0320817 A1    Nov. 9, 2017

(30) Foreign Application Priority Data

Dec. 11, 2014    (MX) .................... MX/a/2014/015226

(51) Int. Cl.
*C07C 309/14*    (2006.01)
*C07C 309/69*    (2006.01)
(Continued)

(52) U.S. Cl.
CPC .......... *C07C 309/14* (2013.01); *C07C 303/22* (2013.01); *C07C 309/69* (2013.01); *C09K 8/54* (2013.01); *C09K 8/584* (2013.01)

(58) Field of Classification Search
None
See application file for complete search history.

(56) References Cited

U.S. PATENT DOCUMENTS

| 3,643,738 A | 2/1972 | Dreher et al. |
| 4,039,336 A | 8/1977 | Sullivan, 3rd et al. |

(Continued)

FOREIGN PATENT DOCUMENTS

| CA | 2723948 | 6/2011 |
| CA | 2828519 | 6/2014 |

(Continued)

OTHER PUBLICATIONS

Masuyama ("Synthesis and Properties of Bis(taurine)Types of Double-chain Surfactants" J. Jpn. Oil Chem. Soc. (Yukagaku), vol. 41, issue 4, p. 301-305, 1992) (Year: 1992).*

(Continued)

*Primary Examiner* — Amy C Bonaparte
(74) *Attorney, Agent, or Firm* — Jason P. Mueller; FisherBroyles, LLP (57) ABSTRACT

The present disclosure is related to obtaining and using sulfobetaine and hydroxysultaine-based geminal zwitteri- (Continued)

a)

b)

onic liquids as wettability modifiers for rocks such as limestone, dolomite, sandstone, quartz or heterogeneous lithologies, under the presence of brines having high content of divalent ions as calcium, magnesium, barium and strontium, at high temperature and high pressure conditions for enhanced oil recovery processes to increase the oil production. The geminal zwitterionic liquids of the present disclosure have also the property of acting as corrosion inhibitors of ferrous metals used in pipelines and equipment for crude oil extraction, production, transport and storage operations. A further advantage shown by zwitterionic liquids derived from their molecular structure is they can be dissolved in distilled water, brine, hydrocarbon solvents, aromatics and alcohols.

14 Claims, 5 Drawing Sheets

(51) Int. Cl.
*C07C 303/22* (2006.01)
*C09K 8/54* (2006.01)
*C09K 8/584* (2006.01)

(56) References Cited

U.S. PATENT DOCUMENTS

| | | | |
|---|---|---|---|
| 4,509,951 | A | 4/1985 | Knapp |
| 4,842,065 | A | 6/1989 | McClure |
| 4,900,458 | A | 2/1990 | Schroeder et al. |
| 5,042,580 | A | 8/1991 | Cullick et al. |
| 5,084,210 | A | 1/1992 | Teeters |
| 5,275,744 | A | 1/1994 | Ho |
| 6,521,028 | B1 | 2/2003 | Frenier |
| 8,105,987 | B2 | 1/2012 | Acosta et al. |
| 2006/0013798 | A1 | 1/2006 | Henry et al. |
| 2009/0023618 | A1 | 1/2009 | Futterer et al. |
| 2011/0138683 | A1 | 6/2011 | Hernandez Altamirano et al. |

FOREIGN PATENT DOCUMENTS

| | | | | |
|---|---|---|---|---|
| MX | | 246603 | 6/2007 | |
| MX | | 254565 | 2/2008 | |
| MX | | 260049 | 8/2008 | |
| MX | | 2010012348 | 11/2010 | |
| MX | | 2009013704 | 6/2011 | |
| MX | | 2012011116 | 3/2014 | |
| MX | | 2012014187 | 6/2014 | |
| WO | WO-2012160187 A1 | * | 11/2012 | ........... A61K 31/205 |

OTHER PUBLICATIONS

The Penguin dictionary of science definition for "zwitterion", downloaded from https://search.credoreference.com/content/entry/penguinscience/zwitterion/0 on Jul. 3, 2019. (Year: 2019).*

Li ("Novel ionic liquid-type Gemini surfactants: Synthesis, surface property and antimicrobial activity" Colloids and Surfaces A: Physicochem. Eng. Aspects, 395, 2012, p. 116-124) (Year: 2012).*

Wu ("Preparation and oil-recovery properties of amino-sulfonate amphoteric Gemini surfactants" Jingxi Yu Zhuanyong Huaxuepin, 2009, vol. 17, issue 21, p. 25-27, including English language translation) (Year: 2009).*

Yoshizawa, Masahiro | "A New Family of Zwitterionic Liquids Arising from a Phase Transition of Ammonium Inner Salts Containing an Ether Bond", Chemistry Letters, vol. 33. No. 12 (2004), pp. 1594-1595.

Podjava, a. | "Liquid Chromatography—Mass Spectrometry of Zwitterionic Liquids", Latvian Journal of Chemistry, No. 1-4 (2010), pp. 102-113.

Fang, Dong et al. | "The Knoevenagel Reaction in water catalyzed by zwitterionic liquids", Monatsh Chem, No. 139 (2008), pp. 799-803.

Zamudio-Rivera, Luis S. et al. | "Carbon Steel Corrosion Control in Hydrogen Sulfide Environments by 1-(2-Hydroxyethyl)-2-Alkyl-Imidazolines and their corresponding Amide Precursors", Journal of Chemical Society of Mexico, vol. 46, No. 4 (2002), pp. 335-340, abstract only.

Olivares-Xometl, O. et al. | "Surface Analysis of inhibitor films formed by imidazolines and amides on mild steel in an acidic environment", Applied Surface Science, No. 252 (2006), pp. 2139-2152.

De Jager, Henk-Jan et al. | "Kinetics of Acid-Catalyzed Hydrolysis of a Polyphosphate in Water", The Journal of Physical Chemistry, No. 102 (1998), pp. 2838-2841.

Austad, T. et al. | "Chemical flooding of oil reservoirs 8. Spontaneous oil expulsion from oil- and water-wet low permeable chalk material by imbibition of aqueous surfactant solutions", Colloids Surf. A: Physicochem. Eng. Aspects, No. 137 (1998), pp. 117-129.

Standnes, D. C. et al.| "Wettability alteration in chalk: 2. Mechanism for wettability alteration from oil-wet to water-wet using surfactants", Journal of petroleum Science and Engineering, No. 28 (2000), pp. 123-143.

* cited by examiner

HYDROXYSULTAINE- AND SULFOBETAINE-BASED GEMINAL ZWITTERIONIC LIQUIDS, METHOD FOR OBTAINING SAME, AND USE THEREOF AS WETTABILITY MODIFIERS HAVING CORROSION INHIBITING PROPERTIES

TECHNICAL FIELD OF THE INVENTION

The present invention is located in the area of multifunctional chemicals applied to the oil industry in enhanced oil recovery processes, specifically in the obtaining and use of geminal zwitterionic liquids hidroxisultaine- and sulfobetaine-base with wettability modifying properties of carbonate rocks or heterogeneous lithology in presence of brines having a high concentration of divalent ions, such as calcium, magnesium, barium and strontium under high temperature and high pressure conditions.

The hidroxisultaine- and sulfobetaine-base geminal zwitterionic liquids of the present invention can act as corrosion inhibitors in crude oil production pipelines.

BACKGROUND OF THE INVENTION

Geminal zwitterionic liquids (1) are a family that is characterized by having hydrocarbon chains (A), a bridge (B) and two polar zwitterionic groups (C).

(1) Chemical structures of some Zwitterionic liquids

The Geminal zwitterionic liquids are neutral compounds that contain formal positive (2 cations) and negative charges (2 anions) at different atoms of the same molecule. They are molecules capable of adapting to different media and therefore they can be designed so that they respond efficiently according to pollutants and operating conditions where they are expected to work.

Below, there are some examples of chemical structures of zwitterionic liquids sulphonate-base, that are reported in the literature (2) [Chemistry Letters, 2004, 33 (12), 1594-1595; Latvian Journal of Chemistry, 2010, (1-4), 102-113; Monatshefte für Chemie, 2008, 139, 799-803].

(2) Chemical structures of some sulfobetaine-base zwitterionic liquids

For the particular case of the increase in the hydrocarbons production after primary and secondary recoveries, the oil reservoir still contains 50-80% of crude oil originally in place. This is due to that the primary and secondary recovery methods efficiency is limited by two factors:

At pore scale, the crude oil can reach such a residual saturation sufficiently low to be found in the form of discontinuous globules trapped by capillary forces.

At reservoir scale, there exist certain areas in which the injected fluid for the secondary recovery does not penetrate, as a result of the low permeability of these zones.

The currently proposed enhanced oil recovery methods are aimed at the solution of the above mentioned problems. The use of wettability modifiers surfactant chemicals is one of the methods most widely used, within these surfactants are cationic, anionic, non-ionic and zwitterionic or mixture of these chemicals.

A wettability modifier is defined as a surfactant that is able to change favorably the reservoir rock affinity. The wettability is a measure of the interaction among the phases presents in the reservoir and is a function of the interfacial chemistry of these phases and determines the tendency of a fluid to move forward or remain adhered to a solid surface in the presence of other immiscible fluids. The rock wettability can be modified naturally by the adsorption of polar compounds, the organic material deposits formation that were originally in oil or by different external agents. Wettability changes affect the capillary pressure, relative permeability, residual oil saturation and irreducible water saturation.

Despite of the continued progress in chemical wettability modifiers development, currently there exist reservoir sites very quiet difficult to handle, mainly because they are naturally fractured reservoirs, which have low matrix permeability, heterogeneous lithologies, high temperatures, above 90° C., high salinity, greater than 60,000 ppm as sodium chloride, and a high content of divalent ions, mainly calcium and magnesium, more than 5000 ppm.

As a result of the just mentioned above, the characterization of the reservoir type of rock, as well as the composition of adsorbed crude oil and its surrounding environment, it is of the utmost importance in designing new wettability modifiers and even to propose molecular structures tolerant to salt and divalent ions saturated brine, mainly calcium and magnesium; those chemicals ought to possess a good diffusion through the medium, generally composed of brine, oil which contains moieties with polar groups with affinity for the rock able to favorably modify the wettability from oil-wet to water-wet.

Globally there are a variety of specific cases of chemicals that have been successfully used to solve those problems, for example anionic surfactants such as sodium alkyl sulfonates or cationic surfactants like alkyl ammonium chlorides, but unfortunately their application is not universal, because of the conditions present in Mexican reservoirs are quite different from other countries, for this reason, the development of more versatile chemicals is of utmost importance, they have to be used in the most adverse known conditions, and they ought to be able to simultaneously solve the greatest number of problems, as for example the corrosion that is directly associated with the use of sea- or connate-water normally used as the solvent of the wettability modifier chemical, that in order to minimize implementation costs to be injected into the reservoir.

In order to increase the crude oil recovery factor, they have been developed wettability modifiers chemicals such as those cited below:

U.S. Pat. No. 5,042,580 (Oil Recovery Process for use in fractured reservoirs) protects an enhanced oil recovery process that involves the injection in the reservoir a Wettability modifier that consisting of a mixture of different types of surfactants like alkyl sulfonate type and chrome salts derived from fatty carboxylic acids.

U.S. Pat. No. 4,509,951 (Enhanced recovery by imbibition process) protects an enhanced recovery process that involves the injecting in the reservoir of a Wettability modifier that consisting of a mixture of different types of products, Within Which are ammonium salts, hydroxides of alkalis metals, alkyl tripolyphosphates and carbonates and bicarbonates of alkali metals.

US. Patent Application 2009/0023618 A1 (Method of Oil Recovery) protects an enhanced recovery process that involves the injecting to the reservoir of a Wettability modifier consisting of a mixture of different types of organophosphorus compounds.

U.S. Pat. No. 4,842,065 (Oil Recovery Process using a Wettability modifying cyclic process) protects an enhanced recovery process that involves the injecting to the reservoir of Wettability modifier that consisting of a mixture of different types of ethoxylates alcohols.

U.S. Pat. No. 3,643,738 (Control of wettability in oil recovery process), protects a process that it allows the change of Wettability through the use of mixtures of petroleum sulfonates.

MX patent 318024 refers to a geminal zwitterionic liquid composition, amino acid-base with wettability modifying properties in enhanced oil recovery processes with structural formula:

(3) Structural formula of geminal zwitterionic liquids of the MX 318024 patent.

It should be noted that the zwitterionic liquids of said application differ from the present invention because they are sulfobetaine and hydroxysultaine type.

In relation to the use as corrosion inhibitors with application in hydrocarbons exploitation and transportation processes the specialized literature mentions that the main families of chemicals that have been used are: 1) 1-heteroalkyl-2-alkyl Imidazolines (Patent MX 254565, Corrosion Inhibitory Composition for Ferrous Metals in Acid Media, MX Patent 260049, Corrosion Inhibitory Composition and Hydrogen Ampoulement to Ferrous Metals in Basic Media) 2) Alkyl Amide Amines (Journal of Chemical Society of Mexico 2002, 46, 4, 335-340, Carbon Steel Corrosion Control in Hydrogen Sulfide Environments by 1-(2-Hydroxyethyl)-2-Alkyl-Imidazolines and their corresponding Amide Precursors; Applied Surface Science 2006, 252, 6, 2139-2152, Surface Analysis of Inhibitor Films Formed by Imidazolines and Amides on Mild Steel in an Acidic Environment), 3) Polyalkylene polyamines (U.S. Pat. No. 4,900,458, Polyalkylenepolyamines as Corrosion Inhibitors; U.S. Pat. No. 4,275,744, Derivatives of Polyalkylenepolyamines as Corrosion Inhibitors) 4) Acetylenic alcohols (U.S. Pat. No. 5,084,210, Corrosion inhibitors), 5) Diacetylenic alcohols (U.S. Pat. No. 4,039,336, Diacetylenic Alcohol Corrosion inhibitors), 6) Quaternary Ammonium Salts (U.S. Pat. No. 6,521,028, Low Hazard Corrosion Inhibitors and Cleaning Solutions Using Quaternary Ammonium Salts), 7) Bis-imidazolines (MX Patent 246603, Multifunctional, Biodegradable and Low Toxicity Corrosion Inhibitors) and 8) Bis-Quaternary Ammonium Salts (U.S. Patent Application 2006/0013798, Bis-Quaternary Ammonium Salt Corrosion Inhibitors).

Also, due to the impact of corrosion phenomenon in the oil industry when there are high salinities and divalent ions concentrations, at international level different institutions and companies have been working on the development of new chemical structures with improved properties, for example U.S. Pat. No. 8,105,987 (Corrosion Inhibitors for an Aqueous Medium) and U.S. Patent No. 2011/0138683 (Gemini Surfactants, Process of Manufacture and Use as Multifunctional Corrosion Inhibitors).

From the above, it is important to remark that in none of the aforementioned references, is referred the use of geminal zwitterionic liquids, hidroxisultaine and sulfobetaine-based neither it is suggested their obtaining process. Nor their use as wettability modifiers with corrosion inhibiting properties, which alter the rock wettability favorably in enhanced oil recovery processes a wide range of rocks such as limestone, dolomite, sandstone, quartz or heterogeneous lithologies, where these zwitterionic liquids may be exposed to brines with high content of divalent ion as they are calcium, magnesium, barium and strontium (150,000 ppm), temperatures up to 220° C.; pressures up to 300 kg/cm$^2$; and they prevent and control the corrosion in pipeline of crude oil production in enhanced oil recovery processes.

BRIEF DESCRIPTION OF THE FIGURES OF THE INVENTION

DESCRIPTION OF THE INVENTION

The present invention relates to obtaining and use of geminal zwitterionic liquids, hidroxisultaine- and sulfobetaine-based, as wettability modifiers of rocks such as limestone, dolomite, sandstone, quartz or heterogeneous lithologies in the presence of crude oil and brine water with high content of divalent ions as calcium, magnesium, barium, and strontium, high temperature and high pressure; to increase oil production in enhanced oil recovery processes.

The geminal zwitterionic liquids based on hydroxysultaine and sulfobetaine of the present invention have also the property of acting as corrosion inhibitors, in extraction, production, transport, and storage operations, properly preventing and controlling the generalized and localized corrosion problems. An additional advantage presented by the zwitterionic liquids of the present invention is that due to its molecular structure, they may be soluble in brine, crude oil or organic solvents such as toluene, xylenes, chloroform and alcohols.

The geminal liquid zwitterionic of the present invention constitute a family characterized by having hydrocarbon chains, a polyether type bridge and two zwitterionic type polar groups which may be hydroxysultain or sulfobetaine type.

The geminal zwitterionic liquids, hidroxisultaine- and sulfobetaine-based of the present invention have the following structural formula:

Where:
R$_1$=is a radical represented by alkyl or alkenyl chain, linear or branched, preferably of 1 to 30 carbon atoms; or an cyclo alkyl or aryl group, preferably of 5 to 12 carbon atoms;

R$_2$=is a radical represented by —H or a alkyl or alkenyl chain, linear or branched, preferably of 1 to 30 carbon atoms; or an cyclo alkyl or aryl group, preferably of 5 to 12 carbon atoms;

R$_3$=—CH$_2$—, —CH$_2$—CH(OH)—;

y=can have values from 0 to 1;

When y is equal to 1:

R$_4$=is a radical represented by —OH n can have values from 1 to 500, depending on the molecular weight of polyether used, where the polyether used is derived from ethylene oxide whose molecular weight is in the range 100 to 20,000 g/mol.

For the development of the present invention a procedure was followed that consists of the following stages: 1) molecular design through computational chemistry, 2) synthesis of branched geminal zwitterionic liquids, 3) spectroscopic characterization of geminal zwitterionic liquids and (4) experimental evaluation of wettability modifiers and corrosion inhibitory properties.

An additional advantage presented by the hidroxisultaine- and sulfobetaine-based geminal zwitterionic liquids of the present invention is that due to its molecular structure, they may be soluble in brine, crude oil or water.

1) Molecular Design by Means of Computational Chemistry

Before going into details, and for clarification purposes, it is worth mentioning that the current trend, involving the development of new chemical products with industrial application, is as the first stage the molecular design by means of computational chemistry, of moieties that will have the potential ability to solve the problems of interest. This molecular design is intended to systematically direct the efforts aimed to the synthesis of new molecules with enhanced properties.

The first thing to determine within molecular design for problems related with wettability modification and corrosion inhibition is:

i) The interaction forces magnitude between the characteristic rock surface of a given reservoir and the polar molecules of high molecular weight in the crude oil, since these data constitute the reference energy that must be overcome by the appropriate insertion of a wettability modifier agent.

ii) It also requires a deep understanding of the wettability modification molecular mechanisms with the objective of suggest a surfactant with the most suitable molecular structure.

iii) In addition, in connection to the viscosity reduction application is required to determine the nature and magnitude of the intermolecular forces that generate oil high viscosity with a high content of polar compounds of large molecular weight such as asphaltenes and resins. These data provide the reference energy that must be overcome by insertion of an appropriate viscosity reducer agent.

iv) Finally, optimal structural parameters that it should include a wettability modifier and viscosity reducer molecule are selected, this from a technical-economic standpoint in order to propose an initial molecular structure to which it calculates the interaction energy with rock surface to determine whether this interaction will be greater or lesser in energy with respect to the polar organic compounds of high molecular weight, which are required to be removed from the surface in such a way to increase the oil recovery factor in the reservoir. In this point the design process can be iterative up to find a molecular species that effectively has an interaction energy with greater than oil polar compounds adsorbed on the rock.

In the specialized literature mentions that the effectiveness of wettability change in rock depends on the ionic nature of surfactant involved involucrado (Colloids Surf. A: Physicochem. Eng. Aspects 1998, 137, 117-129. Austad, T.; Matre, B.; Milter, J.; Saevareid, A.; Oyno, L. *Chemical flooding of oil reservoirs 8. Spontaneous oil expulsion from oil-and water-wet low permeable chalk material by imbibition of aqueous surfactant solutions*; J. Pet. Sci. Eng. 2000, 28, 123-143. Standnes, D. C.; Austad, T. Wettability alteration in chalk: 2. Mechanism for wettability alteration from oil-wet to water-wet using surfactants) and that in oil-wet limestone cores, cationic surfactants have better perform than anionic. It has been proposed that in the case of cationic surfactants, the mechanism through which modify the wettability in an oil wet rock is the formation of ion pairs between the surfactant cationic head of the surfactants and the oil acidic components adsorbed on the carbonate rock surface.

The formation of this ion pairs could remove the layer of crude oil components adsorbed on the rock surface, thus exposing the calcium carbonate rock surface, which is water-wet in origin. In contrast, anionic surfactants form a monolayer on the rock surface through hydrophobic interaction between tails of the surfactant molecules and crude oil components adsorbed on the rock surface. Thus, the rock would be covered by surfactant molecules layer formed with hydrophilic groups on the surface, which could modify the rock wettability characteristics, oil-wet to water-wet.

In the case of the present invention, hidroxisultaine- and sulfobetaine-based geminal zwitterionic liquids have the ability to alter the wettability of carbonate rocks from oil-wet to water-wet through the two mechanisms mentioned above in parallel and thus present more efficiently than cationic or anionic surfactants traditionally they have been used.

In addition, duality charge having in the structure would allow interact effectively with different types of rock and oils, as they may form ionic pairs with species both positive and negative charge.

Just as it was stated in the Background of the Invention, zwitterionic surfactants present significant advantages compared to cationic or anionic surfactants because as zwitterions have both positive and negative charge in its structure, which increases the possibility to interact with rock surfaces with both positively and negatively, charged in contrast with one type of charge surfactants.

In many fields internationally, is present the cases of heterogeneous lithologies, that hinder the enhanced oil recovery process by wettability change, in these cases requires the use of effective wettability modifiers that in contact with different types of rock such as limestone, dolomite, sandstone, quartz or heterogeneous lithologies, even in the presence of brine with high content of divalent ions such as calcium, magnesium, barium and strontium, high temperature and pressure in enhanced oil recovery processes to increase oil production.

From the previous data is seen that the generated branched geminal zwitterionic liquids have advantages over conventional surfactants, used as wettability modifiers in different types of lithologies under high salinity and temperature conditions.

In order to prove the above declared premises, theoretical calculations were performed simulating the adsorption process of polar molecules of high molecular weight on the rock surface originally water-wet with the purpose of determine the adsorption energy that must overcome the wettability modifier molecule; in the same way it was simulated the branched sulfobetaine type geminal zwitterionic liquid adsorption process, corresponding to the present invention, on the same rock which is originally water-wet; then, the adsorption energies are compared for establishing whether or not, from the theoretical viewpoint, if the asphaltene desorption process would be favorable thermodynamically by introducing a wettability modifier of the present invention. The obtained results are described in the following examples:

Example 1

Asphaltene-Calcite Interaction

Figure 1:
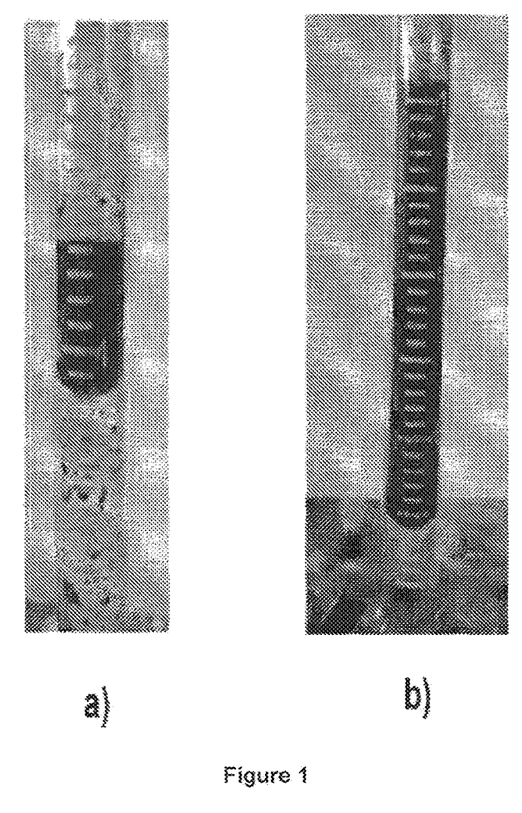
FIG. 1 shows the production of oil in the Amott cell capillary for: a) system that only contains brine, b) a system containing brine and 300 ppm of sulfobetaine-based geminal zwitterionic liquid described in example 2.
Figure 2:
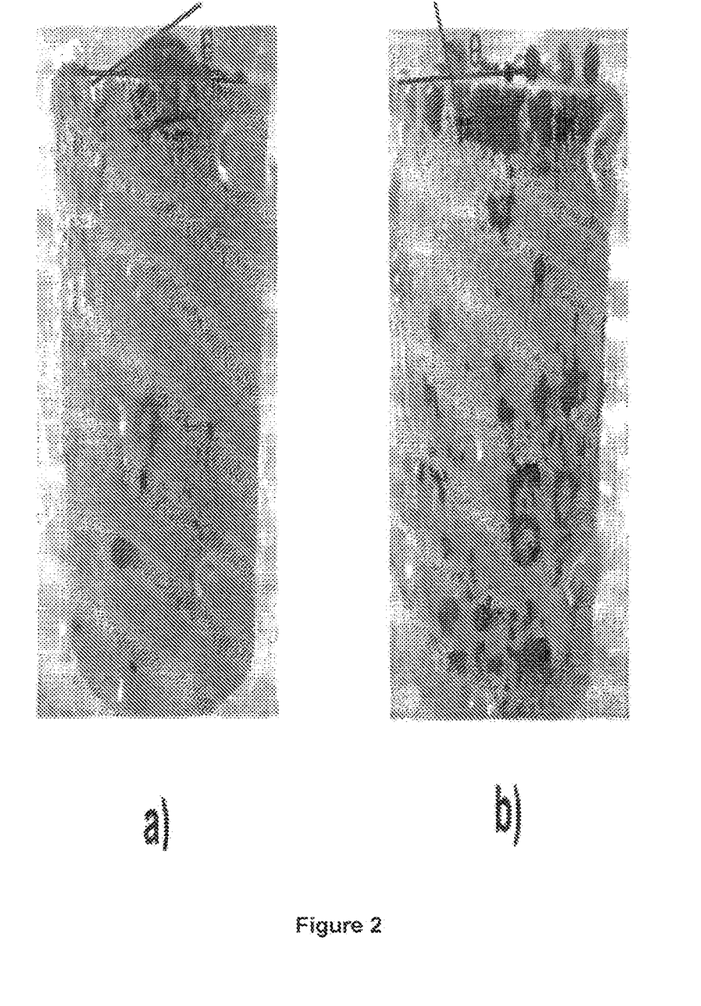
FIG. 2 shows the drop forms: a) system that only contains brine, b) a system containing brine and 300 ppm of ppm of sulfobetaine-based geminal zwitterionic liquid described in example 2.
Figure 3:
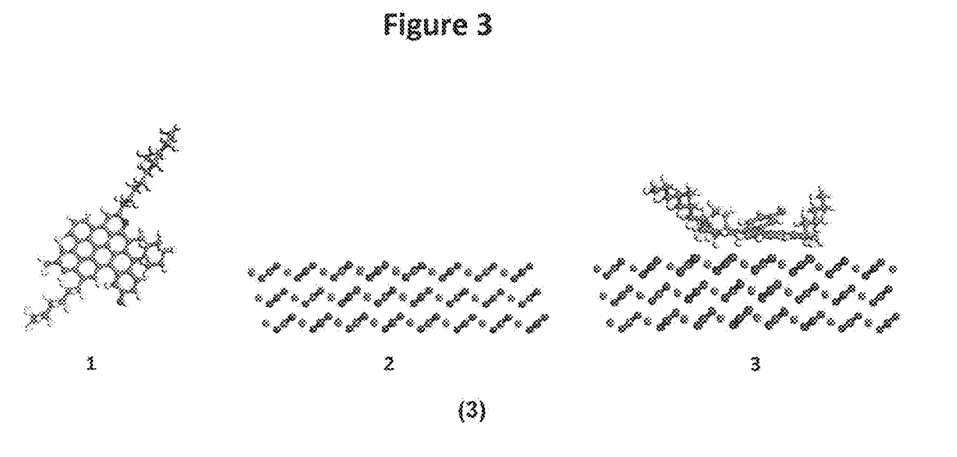
FIGS. 3 and 4 show the asphaltenes average molecular structure model that globally represent their characteristics of heavy oil from the Marine Region in Mexico, the calcite surface geometry ($CaCO_3$), and the adsorption geometry of the product generated from the interaction of asphaltene structure molecular model with calcite surface (CaCO$_3$), for the evaluation described in Example 1.
Figure 4:
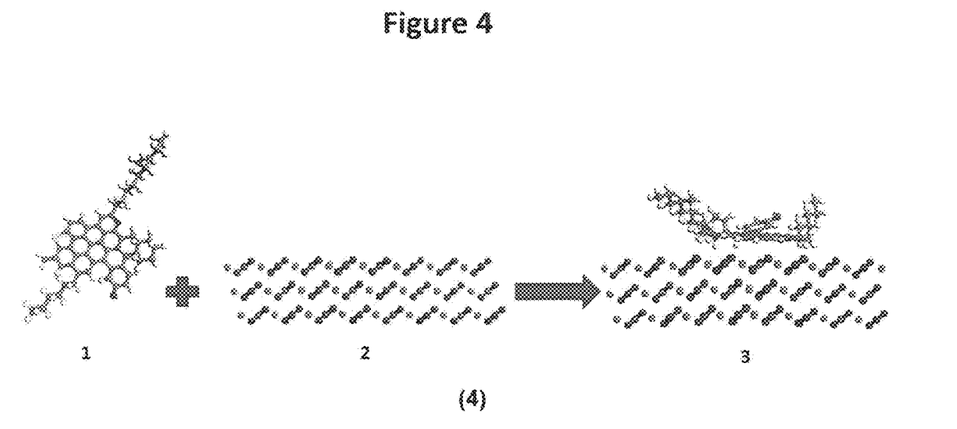

By means of computational chemistry, and using Density Functional Theory methods and LDA-WNV functional, results were optimized in a water-solvated medium (Dielectric constant 78.54). The asphaltenes average molecular structure model that globally represent their characteristics of heavy oil from the Marine Region in Mexico 1, the calcite surface geometry ($CaCO_3$) 2 and the adsorption geometry of the product generated 3 from the interaction of asphaltene structure molecular model 1 with calcite surface ($CaCO_3$) 2 (3) and the energy results for the adsorption process of the asphaltenes molecular model structure 1 on the calcite surface ($CaCO_3$) 2 (4) are shown in FIGS. 3 and 4 and in Table 1 below.

TABLE 1

Energy results obtained for the adsorption of asphaltene molecular model structure 1 on calcite surface ($CaCO_3$) 2 obtained with Density Functional Theory and LDA-VWN functional in a water-solvated medium.

| Molecule or Complex | Density Functional Theory, LDA-VWN functional | |
|---|---|---|
| | Total energy (kcal/mol) | Interaction energy (kcal/mol) |
| 1 | −1,727,746.029 | −188.63 |
| 2 | −70,629,899.29 | |
| 3 | −72,356,833.96 | |

According to the results of Table 1, is noted the adsorption of asphaltenes on the calcite surface would be a thermodynamically favorable process, given the negative sign, with a magnitude of 188.63 kcal/mol. This example simulates the oil recovery in a carbonate rock oil-wettable process which is experimentally attributed to polar compounds adsorption of the oil on the rock over hundreds and thousands of years; and is the energy that must overcome a wettability modifier injected into the reservoir in enhanced recovery process.

Example 2

By means of computational Chemistry and by using quantum chemical methods which employ Density Functional Theory along with the LDA-VWN functional, results were optimized in a water-solvated medium (Dielectric constant 78.54). The asphaltenes average molecular structure model that represents their characteristics of heavy oil from the Marine Region in Mexico (Garcia-Martinez; J.; Tesis de Maestría. 2004) 1, dolomite surface geometry ($CaMg (CO_3)_2$) 4 and the adsorption geometry of the product generated 5 from the interaction of asphaltene structure molecular model 1 with dolomite surface ($CaMg (CO_3)_2$) 4 and the energy results for the adsorption process of the asphaltenes molecular model structure 1 on the calcite surface (CaMg (CO$_3$)$_2$) 4 (6) shown in FIGS. 5 and 6 and in Table 2 below.

TABLE 2

Figure 5:
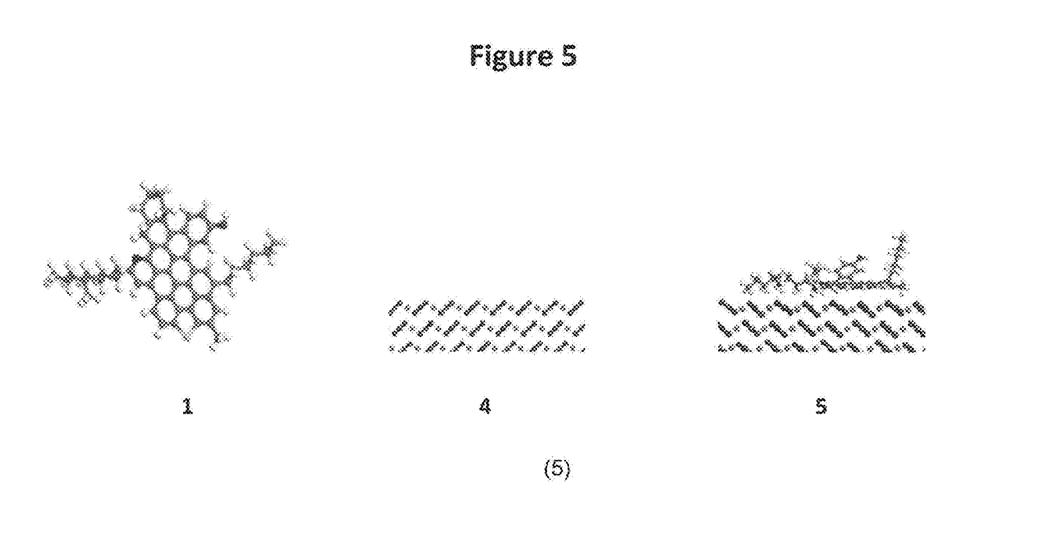
FIGS. 5 and 6 show the asphaltenes average molecular structure model that globally represent their characteristics of heavy oil from the Marine Region in Mexico, the dolimite surface geometry (CaMg (CO$_3$)$_2$), and the adsorption geometry of the product generated from the interaction of asphaltene structure molecular model 1 with dolomite surface (CaMg (CO$_3$)$_2$), for the evaluation described in Example 2.
Figure 6:
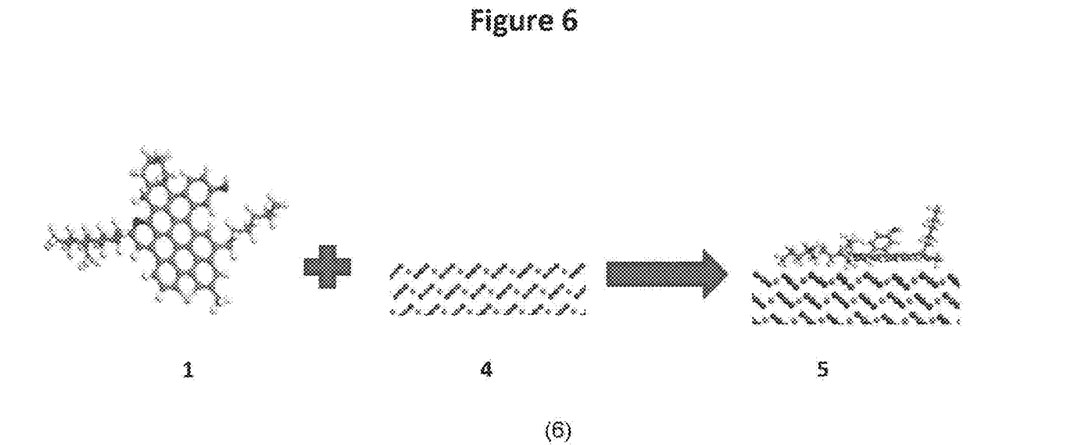

Energy results obtained for the adsorption of asphaltene molecular model structure (1) on dolomite surface (CaMg (CO$_3$)$_2$) 4 obtained with Density Functional Theory and LDA-VWN functional in a water-solvated medium.

| Molecule or Complex | Density Functional Theory, LDA-VVWN functional | |
|---|---|---|
| | Total energy (kcal/mol) | Interaction energy (kcal/mol) |
| 1 | −1,727,746.029 | −178.07 |
| 4 | −52,685,382.68 | |
| 5 | −54,412,756.79 | |

According to the Table 2 results, is noted that the asphaltenes adsorption on the dolomite surface would be a thermodynamically favorable process, with a magnitude of −178.07 kcal/mol.

Example 3

Figure 7:
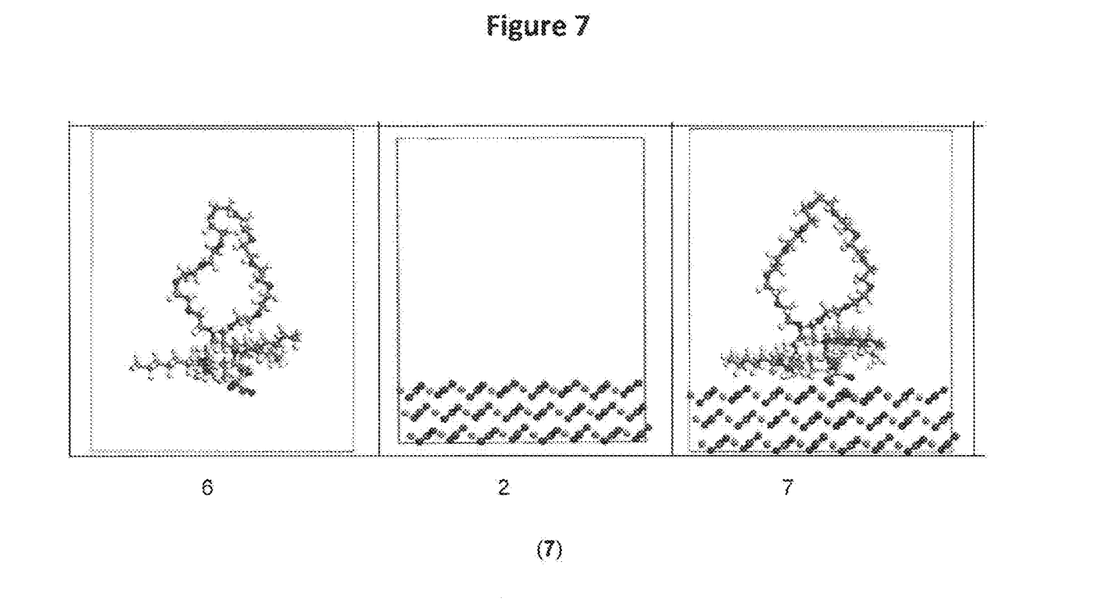
FIG. 7 shows a geminal zwitterionic liquid, sulfobetaine base, calcite surface geometry (CaCO3) and adsorption product geometry generated from the interaction of the zwitterionic liquid molecular structure with the calcite surface (CaCO$_3$), for the evaluation described in Example 3.

By means of computational chemistry, and using Density Functional Theory methods and LDA-VWN functional, the molecular structure geometry were optimized in a water-solvated medium (Dielectric constant 78.54). A geminal zwitterionic liquid, sulfobetaine base of the present invention 6, calcite surface geometry (CaCO3) 2 and adsorption product geometry 7 generated from the interaction of zwitterionic liquid molecular structure 6 with the calcite surface (CaCO$_3$) 2 (7) and the energy results obtained of the adsorption process of the zwitterionic liquid molecular structure 6 on the calcite surface (CaCO$_3$) 2 (8) are shown in FIG. 7 and in Table 3 below.

TABLE 3

Energy results obtained for the adsorption process of a molecular structure of a geminal zwitterionic liquid, sulfobetaine base 6 on calcite surface (CaCO$_3$) 4 obtained with Density Functional Theory and LDA-VWN functional in a water-solvated medium.

| Molecule or Complex | Density Functional Theory, LDA-VWN functional | |
|---|---|---|
| | Total energy (kcal/mol) | Interaction energy (kcal/mol) |
| 6 | −2926939.86 | −151.0772 |
| 2 | −70629859.1 | |
| 7 | −73556950 | |

According to the Table 3 results, is noted that the adsorption of geminal zwitterionic liquid, sulfobetaine base on the calcite surface would be a thermodynamically favorable process, given the negative sign, with a magnitude of 151.08 kcal/mol. Moreover, when comparing this last result with the one presented in the table 1 corresponding to the asphaltene-calcite interaction, must be the zwiterionic liquid-calcite interaction is more favorable or of less energy so it is checked from the theoretical viewpoint that the zwitterionic liquids have the potential to function adequately as wettability modifiers for rocks with high tendency to be oil-wettable such as carbonate rocks.

Example 4

Figure 8:
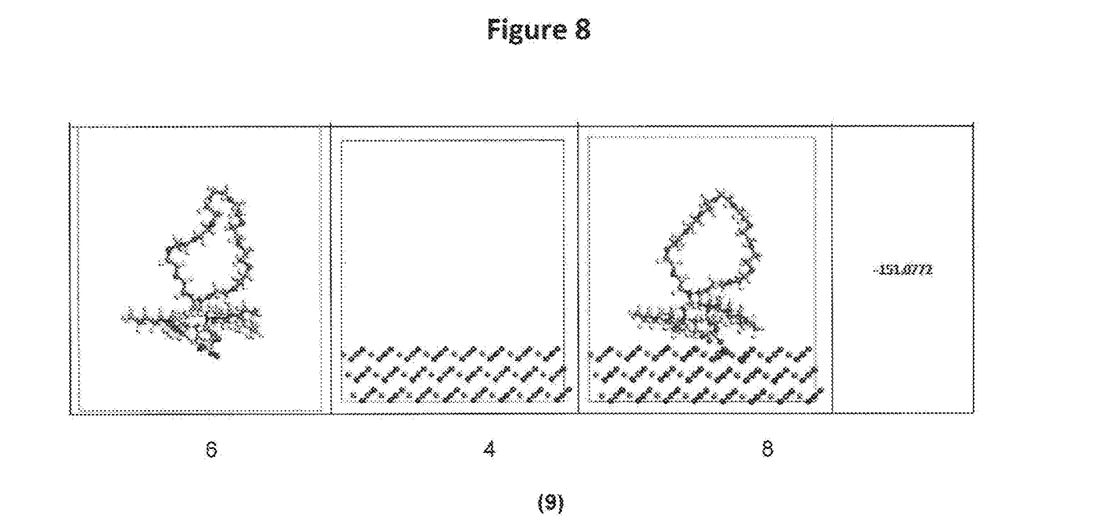
FIG. 8 shows a geminal zwitterionic liquid, sulfobetaine base, dolomite surface geometry (CaMg (CO$_3$)$_2$), and adsorption product geometry generated from the interaction of the zwitterionic liquid molecular structure with dolomite surface geometry (CaMg (CO$_3$)$_2$), for the evaluation described in Example 4.

By means of computational chemistry, and using Density Functional Theory methods and LDA-VWN functional the molecular structure geometry were optimized in a water-solvated medium (Dielectric constant 78.54). A geminal zwitterionic liquid, sulfobetaine base of the present invention 6, dolomite surface geometry (CaMg (CO$_3$)$_2$) 4 and adsorption product geometry 8 generated from the interaction of zwitterionic liquid molecular structure 6 with dolomite surface geometry (CaMg (CO$_3$)$_2$) 4 (9) and the energy results obtained for the adsorption process of the molecular structure of zwitterionic liquid 6 on dolomite surface geometry (CaMg (CO$_3$)$_2$) 4 (10) are shown in FIG. 8 and in Table 4 below.

TABLE 4

Energy results obtained for the adsorption process of a molecular structure of a geminal zwitterionic liquid, sulfobetaine base 6 on dolomite surface (CaMg (CO$_3$)$_2$) 4 obtained with Density Functional Theory and LDA-WVN functional in a water-solvated medium.

| Molecule or Complex | Density Functional Theory, LDA-VWN functional | |
|---|---|---|
| | Total energy (kcal/mol) | Interaction energy (kcal/mol) |
| 6 | −2926943.99 | −176.82325 |
| 4 | −52685348.2 | |
| 8 | −55612469.1 | |

According to the results of Table 4, is noted that the adsorption of geminal zwitterionic liquid, sulfobetaine base, of the present invention, on the dolomite surface would be a thermodynamically favorable process, given the negative sign, with a magnitude of 176.82 kcal/mol. Moreover, when comparing this last result with the one presented in the table 2 corresponding to the asphaltene-dolomite interaction, you have that the zwitterionic liquid-dolomite interaction is more favorable or less energy so it is checked, from the theoretical viewpoint, the zwitterionic liquids have the potential to function adequately as wettability modifiers for rocks with high tendency to be oil-wettable such as carbonate rocks.

2) Synthesis of Geminal Zwitterionic Liquid, Sulfobetaine- and Hidroxisultaine Base Once completed the molecular design stage, the zwitterionic liquids selected are synthesized at laboratory level and subsequently evaluated to ascertain the design details. Thereafter, the performance of the zwitterionic liquids of the present invention was evaluated experimentally as wettability modifiers on carbonate rocks with heavy and light crude oil under conditions of high salinity and high temperature and as corrosion inhibitors under characteristic conditions of crude oil production pipelines.

The germinal zwitterionic liquid, sulfobetaine- and hidroxisultaine base, object of the present invention, are prepared according to the following synthesis route:

Route 1

The synthesis scheme comprises the following:
For route 1:
The first step is to react Polyethylene Glycols of formula I, derived from ethylene oxide with two hydroxyl groups, one at the end and the other at the beginning of the polymer chain, and whose molecular weight is in the range from 100 to 20,000 g/mol; with benzenesulfonyl chloride or tosyl chloride; where the reaction is carried out with a molar relationship 1:1 to 1:4 between polyethylene glycols of formula I and benzenesulfonyl chloride or tosyl chlorides, preferably 1:1.5 to 1:2.8; with an alkaline base of sodium, potassium or cesium, preferably sodium hydroxide; using water as a solvent, tetrahydrofuran, acetonitrile or chloror- form or mixtures thereof; in a reaction time of 1 to 12 hours, preferably of 3 to 8 hours; and at a temperature of 0 to 25° C., preferably of 5 to 20° C.; to form compounds of formula III.

The second stage consists of reacting the compounds of formula III by a nucleophilic substitution with secondary amines of formula IV which $R_1$ and $R_2$ may be alkyl or alkenyl chains; linear or branched, preferably of 1 to 30 carbon atoms; or cycle alkyl or aryl groups, preferably of 5 to 12 carbon atoms and $R_2$ also can be Hydrogen, wherein the reaction is carried out in a molar ratio between the compounds of formula III and IV of 1:1.5 to 1:4, preferably 1:1.8 to 1:2.6; in the presence of solvents such as acetonitrile, chloroform, dimethylformamide, dimethylsulfoxide, acetone or short chain alcohols; in a reaction time from of 6 to 60 hours, preferably 36 hours; and at a temperature of 50 to 150° C.; for obtaining tertiary amines of formula V.

The third stage is the reaction between the compounds of formula V and 2-bromoethane sulfonate of formula VI or sodium 3-chloro-2-hydroxy propane sulfonate of formula VII, in a molar ratio of 1:1.5 to 1:4, preferably 1:1.8 to 1:2.6; the reaction is carried out in the presence of solvents such as water or short-chain alcohols, preferably water; the reaction time, the temperature and the pressure depend of the structure of them compounds of formula V; usually the reaction time varies from 6 to 72 hours, preferably of 12 to 48 hours, temperature of 40 to 180° C., preferably 80 to 130° C., and the pressure is generally atmospheric, to obtain compounds of formula VII: base germinal zwitterionic liquid, sulfobetaine- and hidroxisultaine-base For route 2:
The first step is to react polyethylene glycol diglycidyl ether of formula I, derived from ethylene oxide with two epoxide groups, one at the end and the other at the beginning of the polymer chain, and whose molecular weight is in the range from 100 to 20,000 g/mol; with amines of formula IV which $R_1$ and $R_2$ may be alkyl or alkenyl chains; linear or branched, preferably of 1 to 30 carbon atoms; or cycle alkyl or aryl groups, preferably of 5 to 12 carbon atoms and $R_2$ may be also hydrogen and wherein the reaction is carried out in a molar ratio between the compounds of formula III and IV of 1:1.5 to 1:4, preferably 1:1.8 to 1:2.6; in the presence of solvents such as water or short chain alcohols; in a reaction time from of 4 to 15 hours, preferably 8 hours; and at a temperature of 50 to 150° C.; for obtaining amino alcohols of formula V.

The second stage is the reaction between the compounds of formula V and 2-bromoethane sulfonate of formula VI or sodium 3-chloro-2-hydroxy propane sulfonate of formula VII, in a molar ratio of 1:1.5 to 1:4, preferably 1:1.8 to 1:2.6; the reaction is carried out in the presence of solvents such as water or short-chain alcohols, preferably water; the reaction time, the temperature and the pressure depend of the structure of them compounds of formula V; usually the reaction time varies from of 6 to 72 hours, preferably of 12 to 48 hours, temperature of 40 to 180° C., preferably 80 to 130° C., and the pressure is generally atmospheric, to obtain compounds of formula VII: hidroxisultaine- and sulfobetaine-based geminal zwitterionic liquids.

Below are described some practical examples of branched geminal zwitterionic liquids obtaining, through the above-mentioned reaction schemes to have a better understanding of the present invention, without this limiting its scope.

Example 5

Preparation of germinal zwitterionic liquid, sulfobetaine base (Product 1).

First stage, In a 50 ml round bottom balloon flask containing 5.0 g of an aqueous solution to 17 w % of sodium hydroxide (0.85 g) were added 4.24 g of polyethylene glycol whose number average molecular weight is 600 g/mol, the mixture stirred for 20 minutes. Then, at room temperature (20° C.) and atmospheric pressure very slowly 7.37 g of a solution of tosyl chloride at 40 w % (2.95 g) in tetrahydrofuran were added, keeping the temperature below 25° C. throughout the addition. After completion of addition, the reaction mixture was stirred for about an hour at room temperature and atmospheric pressure, then the reaction mixture was made and extraction of organic phase and evaporated the solvent at reduced pressure, to obtain 6.27 g of product PE-TS (polyether ditosylate) as a viscous clear yellow liquid.

As a second stage, in a 500 ml balloon flask, equipped with a magnetic stirrer, condenser and thermometer were added 1.97 g of dioctylamine, 6.27 g of PE-TS, 4.77 g of potassium carbonate and 18 g of acetonitrile. The reaction mixture was stirred vigorously at reflux temperature and atmospheric pressure for eight hours.

After which time the reaction, the reaction mixture was made and extraction of organic phase and evaporated the solvent at reduced pressure, to obtain 6.18 g of bis-N, N-dioctyl-N-polyether as a viscous amber liquid.

As a third stage, in a flask of 100 ml equipped with a condenser, magnetic stirrer and thermometer, 6.18 g of bis-N, N-dioctyl-N-polyether and 2.77 g of sodium chloroacetate in solution of 50 g of water was added. The reaction mixture was stirred vigorously at a reflux temperature and atmospheric pressure for 48 hours.

When the reaction time was completed, the aqueous phase was separated and evaporated under reduced pressure. The dry product was washing with chloroform to remove by filtration salts present. The organic fraction was evaporated under reduced pressure for obtain 6.84 g of zwitterionic liquid as a viscous amber liquid called Bis N, N-dioctyl-N-polyether sulfobetaine.

The spectroscopic characteristics of Product 1 are the following:

Representative bands of FTIR (cm$^{-1}$): 2,922; 2,853; 1,641; 1,464; 1,221 and 1,098.

Representative chemical shifts of NMR $^1$H (CDCl3), 200 MHz, $\delta$ (ppm): 0.86, 1.28, 1.75, 3.05, 3.27, 3.61 and 3.94 ppm.

Representative chemical shifts of NMR 13C (CDCl3), 50 MHz, $\delta$ (ppm): 13.9, 22.3, 31.1, 52.1, 53.3, 65.4 and 70.4 ppm Example 6

Preparation of germinal zwitterionic liquid, hidroxisultaine base (Product 2).

For this example the product bis-N, N-dioctyl-N-polyether is used and described in second stage of example 7.

In a 100 ml balloon flask, equipped with a magnetic stirrer, condenser and thermometer were added 2 g of bis-N, N-dioctyl-N-polyether and were added in solution 0.86 g of sodium 3-chloro-2-hydroxy propane sulfonate in 15 g of water. The reaction mixture was stirred vigorously at reflux temperature and atmospheric pressure for 72 hours.

When the reaction time was completed, the aqueous phase was separated and evaporated under reduced pressure. The dry product was washing with chloroform to remove by filtration salts present. The organic fraction was evaporated under reduced pressure for obtain 1.4 g of zwitterionic liquid as a viscous amber liquid called bis N, N-dioctyl-N-polyether hydroxysultaine.

The spectroscopic characteristics of Product 2 are:
Representative bands of FTIR (cm$^{-1}$): 3,423; 2,922; 2,853; 1,647; 1,465; 1,222 and 1,098.

Representative chemical shifts of NMR $^1$H (CDCl3), 200 MHz, $\delta$ (ppm): 0.83, 1.24, 1.26, 1.67, 2.99, 3.03, 3.20, 3.25, 3.58 and 3.85.

Representative chemical shifts of NMR $^{13}$C (CDCl3), 50 MHz, $\delta$ (ppm): 13.8, 22.3, 31.0, 52.1, 53.2, 65.5 and 70.3.

Example 7

Preparation of germinal zwitterionic liquid, sulfobetaine base (Product 3).

First stage. In a 50 ml round bottom balloon flask containing 10 g of polyethylene glycol diglycidyl ether whose molecular weight is in the range of 526 g/mol were added 3.5 g of dioctylamine. The reaction mixture was stirred vigorously to temperature of 95° C. and atmospheric pressure for one hours to obtain 13.5 g of bis N, N-dioctyl-N-hydroxy polyether as a viscous yellow liquid.

In a 100 ml balloon flask, equipped with a magnetic stirrer, condenser and thermometer were added 2 g of bis-N, N-dioctyl-N-polyether and were added in solution 0.86 g of sodium 2-bromoethane sulfonate in 15 g of water. The reaction mixture was stirred vigorously at reflux temperature and atmospheric pressure for 72 hours.

When the reaction time was completed, the aqueous phase was separated and evaporated under reduced pressure. The dry product was washing with chloroform to remove by filtration salts present. The organic fraction was evaporated under reduced pressure for obtain 1.4 g of zwitterionic liquid as a viscous amber liquid called bis N, N-dioctyl-N-hydroxy polyether sulfobetaine.

The spectroscopic characteristics of Product 3 are:
Representative bands of FTIR (cm$^{-1}$): 3,423; 2,922; 2,853; 1,647; 1,465; 1,222 and 1,098.

Representative chemical shifts of NMR $^1$H (CDCl3), 200 MHz, $\delta$ (ppm): 0.83, 1.24, 1.26, 1.67, 2.99, 3.03, 3.20, 3.25, 3.58 and 3.85.

Representative chemical shifts of NMR $^{13}$C (CDCl3), 50 MHz, $\delta$ (ppm): 13.8, 22.3, 31.0, 52.1, 53.2, 65.5 and 70.3.

3) Performance Testing of the Branched Geminal Zwitterionic Liquids as Wettability Modifiers For the evaluation of the wettability modifying properties of limestone rocks, dolomite, sandstone, quartz or heterogeneous lithologies, in the presence of brine with high salt content and divalent ions such as calcium, magnesium, barium and strontium, the recovery factor is determined by spontaneous imbibition process in Amott cells using limestone cores, in order to evaluate the wettability modifiers efficiency of the present invention with respect to a reference system without the presence of chemical. For the evaluations are selected Bedford limestone cores composed mainly of calcium carbonate, for being a rock that presents strong adsociones of polar organic compounds of the oil, and therefore, is the most severe case for a wettability modifier, which would be guaranteed that such chemicals would function adequately in other rock with less tendency to be oil-wettable.

The test method is described below.
Recovery factor determination by spontaneous imbibition process in limestone cores through Amott cells.

The testing method consists in measure the amount of crude oil recovered from carbonate cores rock, initially oil-saturated due to spontaneous imbibition processes by water; in Amott cells at constant temperature and atmospheric pressure.

Elements required for the test:
Amott cells.
Controlled temperature recirculation device.
Limestone core of 3.81 cm diameter×7 cm long, permeabilities and porosities known.
Photographic camera.
Crude oil.
Connate water with high salinities.
Glass equipment for SOXHLET extraction.
Glass volumetric materials.
Convection oven.
Test Procedures:

1) Submit rock cores (dolostone, limestone or sandstone) to hydrocarbon extraction processes with different organic solvents in a SOXHLET system. The extraction processes are carried out continuously, sequentially or by reflux, using as solvents: a) Hexane b) Xylene, c) Chloroform, d) Methanol, e) Hexane, f) Xylene and g) Chloroform. The duration of each extraction stage is one day and the time for the entire process is 7 days.

2) Determine the absolute permeability to helium in cores and effective porosity.

3) Dry the rock cores in a stove at a temperature of 100° C. and record the weight once a constant weight is reached.

4) Put the rock cores in contact with dead oil originating from the reservoir of interest for 24 hours at the required temperature and at a pressure of 140±5 psi, in an aging cell.

5) Strain the rock cores saturated with dead oil at atmospheric temperature and pressure until no dropping is observed. The straining process lasts about 12 hours and a number 200 wire mesh is used for this purpose.

6) Weigh rock cores soaked with dead oil and, by weight difference, obtain the amount of oil adsorbed by the porous medium.

7) Prepare 500 mL of the aqueous solution (connate water) to be assessed at the concentration of chemical product required in the test.

8) Place a rock core in the Amott cell and add carefully 350 mL of the chemical product to be assessed at the required concentration.

9) Increase the temperature of the system to the temperature desired for the assessment of the performance of the chemical product or sample under study and maintain the same for the period of time at which the recovery factor is intended to be determined under the temperature and salinity conditions.

9) Quantify the amount of oil produced due to spontaneous water imbibition processes under study conditions and determine the recovery factor according to the following equation:

$$R_f = O_r/O_a \times 100$$

Where:
Rf=Recovery factor; Or=Recovered oil; Oa=Original oil adsorbed on the porous media.

Example 8

Evaluation results of spontaneous imbibition process by wettability change using light crude oil.

According to the methodology described above, was placed in the Amott cells carbonated cores that were impregnated with light oil (see table 5) and in contact with solutions of product 1, 2 and 3 in connate water 1 (see table 6) with duration of 15 days to 90° C.

TABLE 5

SARA analysis, acid and basic total number data of light crude oil.

| Oil | SARA | | | | Total acid number (TAN) | Total basic number (TBN) |
| --- | --- | --- | --- | --- | --- | --- |
| | Saturated | Aromatic | Resins | Asphaltenes | | |
| Light oil | 30.68 | 28.62 | 39.35 | 1.32 | 0.21 | 1.7 |

TABLE 6

Connate water 1 properties.

| Physical properties | | | |
| --- | --- | --- | --- |
| Temperature | 20° C. | | |
| pH | 7.65 | @ 20° C. | |
| Density | 1.0043 | g/cm³ @ 20° C. | |
| Conductivity | | µS/cm @ 20° C. | |
| Turbidity | 4 FTU | | |

| Chemical properties | | | | | |
| --- | --- | --- | --- | --- | --- |
| Cations | (mg/L) | (meq/L) | Anions | (mg/L) | (meq/L) |
| Sodium (Na⁺) | 1 703.66 | 74.116 | Chlorides (Cl⁻) | 3 200.00 | 90.260 |
| Potassium (K⁺) | — | — | Sulphates (SO₄⁼) | 350.00 | 7.287 |
| Calcium (Ca⁺⁺) | 416.00 | 20.758 | Carbonates (CO₃⁼) | 0.00 | 0.00 |
| Magnesium (Mg⁺⁺) | 106.95 | 8.799 | Bicarbonates (HCO₃⁻) | 405.04 | 6.638 |
| Iron (Fe⁺⁺) | 0.06 | 0.002 | Hydroxides (OH⁻) | — | — |
| Manganese (Mn⁺⁺) | — | — | Nitrites (NO₂⁻) | — | — |
| Barium (Ba⁺⁺) | 35.00 | 0.510 | Nitrates (NO₃⁻) | — | — |
| Strontium (Sr⁺⁺) | — | — | Phosphates (PO₄⁻³) | — | — |
| Total: | 2261.88 | 104.186 | Total: | 3 955.04 | 104.186 |

| Dissolved and suspended solids | | | |
| --- | --- | --- | --- |
| | (mg/L) | | (mg/L) |
| Total solids | — | Total hardness as CaCO₃ | 1 480.00 |
| Total Dissolved Solids (TDS) | 6216.92 | Calcium hardness as CaCO₃ | 1 040.00 |
| Total Dissolved Solids (SST) | — | Magnesium hardness as CaCO₃ | 440.00 |
| Fats and oils | — | Alkalinity to the "F" as CaCO₃ | 0.00 |

TABLE 6-continued

| Connate water 1 properties. | | | |
|---|---|---|---|
| Soluble silica | — | Alkalinity to the "M" as CaCO$_3$ | 332.00 |
| Ferric oxide | — | Salinity as NaCl | 5 275.00 |
| Acidity as | — | Stability Index | 0.288 10 |
| | | Tendency | Encrusting |

Table 7 shows the recovery data obtained in the Amott cells for products 1, 2 and 3 at concentration of 300 mg/L. Brine 1 was used without additives as reference.

TABLE 7

| Light oil recovery results in Amott cells. | | | |
|---|---|---|---|
| Concentration of Product (mg/L) | Grams of oil impregnated | Grams of Total Oil Recovered | Percent recovery |
| Reference | 12.2874 | 4.5796 | 37.27 |
| 1 | 12.1547 | 6.3253 | 52.04 |
| 2 | 11.8760 | 6.0987 | 51.35 |
| 3 | 11.5244 | 5.6878 | 49.35 |

From the results of Table 7 it is possible to observe that hidroxisultaine- and sulfobetaine-based geminal zwitterionic liquids (products 1, 2 and 3) recover about 1.5 times more light crude oil than the reference therefore functioning properly as wettability modifiers in spontaneous imbibition processes.

Example 9

Evaluation of a spontaneous imbibition process due to wettability change by using a heavy crude oil.

According to the methodology described above, it was placed in the Amott cells heavy oil-impregnated carbonate cores in contact to products 1 and 2 in solution with connate water 2 at a 300 mg/L concentration.

The properties of both the heavy crude oil and the connate water 2 are shown in Tables 8 and 9, respectively.

TABLE 8

| SARA analysis as well as total acid and base numbers for heavy oil. | | | | | | |
|---|---|---|---|---|---|---|
| | SARA | | | | Total acid number (TAN) | Total base number (TBN) |
| Oil | Saturated | Aromatic | Resins | Asphaltenes | | |
| Heavy oil | 13.4 | 24.76 | 51.01 | 10.44 | 1.83 | 2.12 |

TABLE 9

| Physicochemical properties of the brine 2. | | | | | |
|---|---|---|---|---|---|
| Physical properties | | | | | |
| Temperature | 20° C. | | | | |
| pH | 6.68 | @ 20° C. | | | |
| Density | 1.0216 | g/cm$^3$ @ 20° C. | | | |
| Conductivity | 45,600 | µS/cm @ 20° C. | | | |
| Turbidity | 15 FTU | | | | |
| Chemical properties | | | | | |
| Cations | (mg/L) | (meq/L) | Anions | (mg/L) | (meq/L) |
| Sodium (Na$^+$) | 11,630.06 | 505.907 | Chlorides (Cl$^-$) | 22,000.00 | 620.540 |
| Potassium (K$^+$) | — | — | Sulphates (SO$_4^=$) | 825.00 | 17.177 |
| Calcium (Ca$^{++}$) | 1,976.00 | 98.603 | Carbonates (CO$_3^=$) | 0.00 | 0.00 |
| Magnesium (Mg$^{++}$) | 427.86 | 35.197 | Bicarbonates (HCO$_3^-$) | 122.00 | 1.999 |
| Iron (Fe$^{++}$) | 0.25 | 0.009 | Hydroxides (OH$^-$) | — | — |
| Manganese (Mn$^{++}$) | — | — | Nitrites (NO$_2^-$) | — | — |
| Barium (Ba$^{++}$) | — | — | Nitrates (NO$_3^-$) | — | — |
| Strontium (Sr$^{++}$) | — | — | Phosphates (PO$_4^{-3}$) | — | — |
| Total: | 14,034.41 | 639.716 | Total: | 22,947.00 | 639.716 |
| Dissolved and suspended solids | | | | | |
| | (mg/L) | | | (mg/L) | |
| Total solids | — | | Total hardness as CaCO$_3$ | 6,700.00 | |
| Total Dissolved Solids (TDS) | 36,981.41 | | Calcium hardness as CaCO$_3$ | 4,940.00 | |
| Total Dissolved Solids (TSS) | — | | Magnesium hardness as CaCO$_3$ | 1,760.00 | |
| Fats and oils | — | | Alkalinity to the "F" as CaCO$_3$ | 0.00 | |
| Soluble silica | — | | Alkalinity to the "M" as CaCO$_3$ | 100.00 | |
| Ferric oxide | — | | Salinity as NaCl | 36,265.59 | |
| Acidity as | — | | Stability Index | −0.71714 | |
| | | | Tendency | Corrosive | |

Table 10 shows the results obtained from Amott cells containing carbonate cores in contact with solutions of sulfobetaine and hidroxisultaine-based geminal zwitterionic liquids (Products 1 and 2) at a 300 mg/L concentration in brine 2 and using heavy crude oil.

TABLE 10

Heavy oil recovery results in Amott cells.

| Chemical | Grams of impregnated oil | Grams of Total Recovered Oil | Recovery Percentage |
|---|---|---|---|
| Reference | 6.8124 | 0.8364 | 12.2776 |
| 1 | 6.8124 | 0.8364 | 12.2776 |
| 2 | 6.8124 | 0.8364 | 12.2776 |

From results of Table 10 it is possible to observe that the sulfobetaine-based geminal zwitterionic liquid (Product 1) recovers about 3 times more heavy crude oil than the reference, and the hydroxysultaine-based zwitterionic liquid (Product 2) recovers about 1.5 times more oil than the reference. So, the sulfobetaine and hydroxysultaine-based branched geminal zwitterionic liquids function adequately as wettability modifiers in spontaneous imbibition processes.

Corrosion inhibition efficiency determination through the NACE 1D-182 method.

The NACE 1D-182 method is a gravimetric test commonly called dynamic wheel (wheel test) that simulates the corrosive environment characteristic of the oil production; it is a dynamic procedure developed for fluids (oil, water and inhibitor).

Equipment and Reagents for Tests a) Dynamic evaluator for corrosion inhibitors with temperature controller, 30-rpm stirrer speed and capacity for 52 bottles of 180 ml.
b) 200-ml bottles.
c) SAE 1010 carbon steel coupons having 1"×0.5"×0.010" dimensions.
d) Glassware for the preparation of the corrosive environment. It consists of a 2 L glass reactor equipped with a cooling bath, a mechanical stirrer, a bubbler for gas (nitrogen and hydrogen sulfide), and has an outlet joined to two in series-connected traps (the first one is charged with sodium hydroxide in pellet form and the second one with a 20% sodium hydroxide solution), so hydrogen sulfide does not contaminate the environment.
e) Potentiometer for pH measuring.

The test conditions are shown in Table 11.

TABLE 11

Test conditions.

| | |
|---|---|
| Temperature | 60° C. |
| Aqueous medium | Synthetic brine with 600 ± 50 ppm of $H_2S$ |
| Test time | 46 hours |
| Organic medium | Kerosene |
| Brine/organic medium volume ratio | 90/10 |
| Test volume | 180 mL |
| Medium pH | 4 |
| Corrosion witness (metal coupons) | SAE 1010 steel |

The composition of brine 3 is shown in Table 12:

TABLE 12

Composition of the brine 3.

| Salts | Amount (g/L) |
|---|---|
| NaCl | 60.0 |
| $CaCl_2 \cdot H_2O$ | 6.0 |
| $MgCl_2 \cdot 6H_2O$ | 10.48 |
| $Na_2SO_4$ | 3.5 |

Results.

The weight difference of the coupons before and after they have been exposed to the corrosive liquid during 46 hours is a direct indication of the metal lost due to the corrosion.

The efficiency as a corrosion inhibitor is obtained by comparing the corrosion speed of the reference or blank with the speed of the witness having a determined corrosion inhibitor concentration, through the following formula (2):

$$\text{Efficiency \%} = (V_0 - V)/V_0 \times 100$$

where $V_0$ is the corrosion velocity of the reference coupon (blank), and V is the corrosion velocity of the coupon having the corrosion inhibitor.

Table 13 shows the results for the Products 1 and 2 used at different concentrations.

TABLE 13

Results of the corrosion rate and the efficiency.

| Chemical | Concentration (ppm) | Corrosion velocity (mpy)* | Efficiency, (%) |
|---|---|---|---|
| Reference | 0 | 32.9 | 0 |
| 1 | 50 | 2.8 | 91.4 |
| 1 | 100 | 2.0 | 93.8 |
| 2 | 50 | 2.9 | 90.9 |
| 2 | 100 | 2.8 | 91.4 |

*mpy: thousandths of an inch per year.

What is claimed is:

1. A process to obtain hydroxysultaine- and sulfobetaine-based geminal zwitterionic liquids, wherein the process is carried out to the following synthesis scheme:

and wherein the synthesis comprises the following steps:
the first step comprises reacting polyethylene glycols of the formula I with benzenesulfonyl chloride or tosyl chloride of the formula II, wherein the reaction is carried out in a reaction time from 1 hour to 12 hours, resulting in a compound of formula III;
the second step comprises reacting the compound of the formula III through a nucleophilic substitution with primary or secondary amines of the formula IV, resulting in amino alcohols of formula V; and
the third step comprises obtaining sulfobetaine and hydroxysultaine-based geminal zwitterionic liquids of the formula VII by reacting the amino alcohols of the formula V with sodium 2-bromoethane sulfonate or sodium 3-chloro-2-hydroxypropane sulfonate of the formula VI; and wherein in all of the formulae above, $R_1$ is a radical represented by an alkyl or alkenyl, linear or branched chain having 1 to 30 carbon atoms, or a cycloalkyl or aryl group having from 5 to 12 carbon atoms; $R_2$ is a radical represented by —H; an alkyl or alkenyl, linear or branched chain having from 1 to 30 carbon atoms; or a cycloalkyl or aryl group, having from 5 to 12 carbon atoms; y is 0 or 1; and n is a value from 1 to 500 depending on the molecular weight of the polyether used to prepare the sulfobetaine or hydroxysultaine, wherein the polyether is derived from ethylene oxide and has a molecular weight in the range of 100 to 20,000 g/mol.

2. The process according to claim 1, wherein the step 1 reaction of the synthesis is carried out with a molar ratio of formula I to formula II of 1:1 to 1:4.

3. The process according to claim 2, wherein the step 1 reaction of the synthesis is carried out in a basic medium comprising sodium, potassium or cesium hydroxide.

4. The process according to claim 2, wherein the step 1 reaction of the synthesis further comprises a solvent selected from the group consisting of water, tetrahydrofuran, chloroform, acetonitrile, and mixtures thereof.

5. The process according to claim 1, wherein the step 1 reaction of the synthesis is carried out at a temperature from 0° C. to 25° C.

6. The process according to claim 1, wherein the step 2 reaction of the synthesis is carried out with a molar ratio between the compounds of the formula III and the secondary amines of the formula IV from 1:1.5 to 1:4.

7. The process according to claim 1, wherein the step 2 reaction of the synthesis for the preparation of the amino alcohols of the formula V is carried out in presence of a solvent, wherein the solvent is selected from acetonitrile, chloroform, dimethylformamide, dimethylsulfoxide, acetone, or short chain alcohols.

8. The process according to claim 1, wherein the step 2 reaction of the synthesis for preparation of amino alcohols of the formula V is carried out in a reaction time from 5 hours to 60 hours.

9. The process according to claim 1, wherein the step 2 reaction of the synthesis for preparation of amino alcohols of the formula V is carried out at a temperature from 50° C. to 150° C.

10. The process according to claim 1, wherein the step 3 reaction of the synthesis between the amino alcohols of the formula V with sodium 2-bromoethane sulfonate or sodium 3-chloro-2-hydroxypropane sulfonate of the formula VI is carried out with a molar ratio of formula V to formula VI of 1:1.5 to 1:4.

11. The process according to claim 1, wherein the step 3 reaction of the synthesis for preparation of compounds of the formula VII can be carried out in the absence or presence of a solvent, wherein the solvent is selected from water, alcohols, aromatics, or inert hydrocarbon solvents.

12. The process according to claim 1, wherein the reaction time of the step 3 reaction of the synthesis ranges from 6 hours to 72 hours.

13. The process according to claim 1, wherein the temperature of the step 3 reaction of the synthesis ranges from 40° C. to 180° C.

14. The process according to claim 1, wherein the pressure of the step 3 reaction of the synthesis ranges from 585 mmHg to 760 mmHg.

* * * * *